US00PP28826P3

(12) United States Plant Patent
van den Haak

(10) Patent No.: US PP28,826 P3
(45) Date of Patent: Dec. 26, 2017

(54) ***ECHINACEA* PLANT NAMED 'APECSSIMA'**

(50) Latin Name: *Echinacea hybrida*
Varietal Denomination: Apecssima

(71) Applicant: Jelle van den Haak, Amsterdam (NL)

(72) Inventor: Jelle van den Haak, Amsterdam (NL)

(73) Assignee: Gootjes-Allplant B.V., Schagen (NL)

( * ) Notice: Subject to any disclaimer, the term of this patent is extended or adjusted under 35 U.S.C. 154(b) by 39 days.

(21) Appl. No.: 14/999,193

(22) Filed: Apr. 8, 2016

(65) Prior Publication Data

US 2017/0295708 P1 Oct. 12, 2017

(51) Int. Cl.
*A01H 5/02* (2006.01)

(52) U.S. Cl.
USPC ..... Plt./428

(58) Field of Classification Search
USPC ..... Plt./263.1, 428
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Echinacea* plant named 'Apecssima', characterized by its upright and relatively compact plant habit; moderately vigorous growth habit; freely branching habit; strong flowering stems; numerous large single-type inflorescences with red purple-colored ray florets and dark orange-colored receptacle spines; and good garden performance.

2 Drawing Sheets

Botanical designation: *Echinacea hybrida.*
Cultivar denomination: 'APECSSIMA'.

BACKGROUND OF THE INVENTION

The present invention relates to a new and distinct cultivar of *Echinacea* plant, botanically known as *Echinacea hybrida*, and hereinafter referred to by the name 'Apecssima'.

The new *Echinacea* plant is a product of a planned breeding program conducted by the Inventor in Andijk and Hazerswoude-Dorp, The Netherlands. The objective of the breeding program is to develop new vigorous *Echinacea* plants with unique and attractive ray floret coloration.

The new *Echinacea* plant originated from an open-pollination in July, 2013 in Andijk, The Netherlands of a proprietary selection of *Echinacea hybrida* identified as code number 009-12-K083-01, not patented, as the female, or seed, parent with an unknown selection of *Echinacea hybrida* as the male, or pollen, parent. The new *Echinacea* plant was discovered and selected by the Inventor as a single flowering plant from within the progeny of the stated open-pollination grown in a controlled greenhouse environment in Hazerswoude-Dorp, The Netherlands in August, 2014.

Asexual reproduction of the new *Echinacea* plant by tissue culture in a controlled environment in Andijk, The Netherlands since 2015 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Apecssima'. These characteristics in combination distinguish 'Apecssima' as a new and distinct *Echinacea* plant:

1. Upright and relatively compact plant habit.
2. Moderately vigorous growth habit.
3. Freely branching habit.
4. Strong flowering stems.
5. Numerous large single-type inflorescences with red purple-colored ray florets and dark orange-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are not as vigorous as plants of the female parent selection.
2. Plants of the new *Echinacea* and the female parent selection differ in ray floret color as plants of the female parent selection have pink-colored ray florets.
3. Inflorescences of plants of the new *Echinacea* have more ray florets than inflorescences of plants of the female parent selection.

Plants of the new *Echinacea* can be compared to plants of *Echinacea* spp. 'Glowing Dream', disclosed in U.S. Plant Pat. No. 24,329. In side-by-side comparisons, plants of the new *Echinacea* differ primarily from plants of 'Glowing Dream' in the following characteristics:

1. Plants of the new *Echinacea* and 'Glowing Dream' differ in stem color as plants of 'Glowing Dream' have darker green-colored stems.
2. Plants of the new *Echinacea* have broader leaves than plants of 'Glowing Dream'.

3. Ray florets of plants of the new *Echinacea* are more horizontal than and not as drooping as ray florets of plants of 'Glowing Dream'.
4. Plants of the new *Echinacea* and 'Glowing Dream' differ in ray floret color as plants of 'Glowing Dream' have deep coral pink-colored ray florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Apecssima' grown in a container.

The photographs on the second sheet are close-up views of typical inflorescences (upper photograph) and typical leaves (lower photograph) of 'Apecssima'.

DETAILED BOTANICAL DESCRIPTION

The aforementioned photographs and following observations and measurements describe plants grown during the summer in 17-cm containers in an outdoor nursery in Mijdrecht, The Netherlands and under cultural practices typically used in commercial *Echinacea* production. During the production of the plants, day temperatures ranged from 18° C. to 30° C. and night temperatures ranged from 8° C. to 18° C. Plants were pinched eight weeks after planting and were six months old when the photographs and description were taken. In the following description, color references are made to The Royal Horticultural Society Colour Chart, 2007 Edition, except where general terms of ordinary dictionary significance are used.

Botanical classification: *Echinacea hybrida* 'Apecssima'.

Parentage:

*Female parent*.—Proprietary selection of *Echinacea hybrida* identified as code number 009-12-K083-01, not patented.

*Male parent*.—Unknown selection of *Echinacea hybrida*, not patented.

Propagation:

*Type*.—By tissue culture.

*Time to initiate roots, summer*.—About twelve days at temperatures about 20° C.

*Time to initiate roots, winter*.—About 16 days at temperatures about 20° C.

*Time to produce a rooted young plant, summer*.—About 36 days at temperatures about 18° C.

*Time to produce a rooted young plant, winter*.—About 42 days at temperatures about 18° C.

*Root description*.—Thick, fleshy; typically white in color, actual color of the roots is dependent on substrate composition, water quality, fertilizer type and formulation, substrate temperature and physiological age of roots.

*Rooting habit*.—Moderately freely branching; sparse.

Plant description:

*Plant form and growth habit*.—Herbaceous perennial; upright and relatively compact plant habit, inverted triangle; freely basal branching habit with about eight lateral branches developing per plant; moderately vigorous growth habit.

*Plant height*.—About 56.4 cm.

*Plant diameter or spread*.—About 45.5 cm.

*Lateral branches*.—Length: About 33.1 cm. Diameter: About 5 mm. Internode length: About 3.6 cm. Aspect: Erect to about 25° from vertical. Strength: Strong. Texture: Densely pubescent; strigose, rough. Color: Close to 144A; stems exposed to direct sunlight are tinged with close to 200B.

Leaf description:

*Arrangement*.—Alternate, simple.

*Length*.—About 10 cm.

*Width*.—About 4.7 cm.

*Shape*.—Ovate to narrowly ovate.

*Apex*.—Acute to narrowly acute.

*Base*.—Attenuate.

*Margin*.—Entire; slightly undulate.

*Texture and luster, upper and lower surfaces*.—Moderately to densely pubescent, strigose and rough; slightly glossy.

*Venation pattern*.—Pinnate.

*Color*.—Developing leaves, upper surface: Close to 137A to 137B. Developing leaves, lower surface: Close to 137D. Fully expanded leaves, upper surface: Close to N137A; venation, close to 145A. Fully expanded leaves, lower surface: Close to 137C; venation, close to 145A.

*Petioles, basal leaves*.—Length: About 5.4 cm. Diameter: About 2 mm by 3 mm. Texture, upper surface: Glabrous. Texture, lower surface: Mostly glabrous; midvein, moderately pubescent. Color, upper surface: Center, close to 144B; towards the margins, close to N137A. Color, lower surface: Center, close to 144B; towards the margins, close to 137A.

Inflorescence description:

*Appearance*.—Large single-type inflorescences with ray and disc florets arranged on a capitulum; inflorescences positioned upright above the foliar plane on mostly upright and strong peduncles.

*Flowering habit*.—Freely flowering habit with about 24 inflorescences per plant.

*Fragrance*.—Faintly; sweet, slightly acidic and pleasant.

*Time to flower*.—Plants flower continuously from mid-July to late November in The Netherlands.

*Inflorescence longevity*.—Inflorescences maintain good substance for about three weeks on the plant; inflorescences persistent.

*Inflorescence buds*.—Height: About 2.3 cm. Diameter: About 2.7 cm. Shape: Flattened globular. Color: Close to 143A to 143B; ray florets, close to 173A, towards the apex, close to 150A to 150B.

*Inflorescence size*.—Diameter: About 10.3 cm. Depth (height): About 2.9 cm. Disc diameter: About 3.6 cm.

*Receptacles*.—Height: About 1 cm. Diameter: About 1.1 cm. Color: Close to 155A.

*Ray florets*.—Quantity and arrangement: About 24 arranged in a single whorl at the base of the receptacle. Length: About 4.4 cm. Width: About 1.5 cm. Shape: Elliptic to oblong or obovate. Apex: Praemorse. Base: Cuneate. Margin: Entire. Texture and luster, upper surface: Glabrous; velvety and matte. Texture and luster, lower surface: Sparsely pubescent; moderately glossy. Aspect: Horizontal to slightly upright, about 10° from horizontal. Color: When opening, upper surface: Close to 63A to 63B. When opening, lower surface: Close to 60D. Fully opened, upper surface: Close to 61B and 67A; with development, color becoming closer to 60B. Fully opened, lower surface: Close to 60B and 60C; with development, color becoming closer to 60C.

*Disc florets*.—Quantity and arrangement: About 180 per inflorescence, arranged spirally at the center of the inflorescence. Length: About 1.2 cm. Diameter: About 3 mm. Shape: Tubular; proximally, 20% free, not fused. Apex: Acute. Base: Fused. Margin: Entire. Texture and luster, inner and outer surfaces: Smooth, glabrous; glossy. Color, when opening, inner and outer surfaces: Apex: Close to 177A. Mid-section: Close to 146B strongly tinged with close to 177A. Base: Close to 146B. Color, fully opened, inner and outer surfaces: Apex: Close to 146A. Mid-section and base: Close to 146C.

*Receptacle spines*.—Quantity: One per disc floret. Shape: Acicular. Apex: Acute. Base: Attenuate. Texture and luster: Smooth, glabrous; glossy. Color: Apex: Proximally, close to 23A; distally, close to 34A. Mid-section: Close to 143C. Base: Close to 145C to 145D.

*Involucral bracts*.—Quantity per inflorescence: About 68 arranged in about four whorls. Length: About 8 mm. Width: About 3 mm. Shape: Ovate to narrowly ovate. Apex: Acute. Base: Cuneate. Margin: Entire. Texture and luster, upper surface: Smooth, glabrous; dull. Texture and luster, lower surface: Moderately pubescent; dull. Color, upper surface: Close to 144B; towards the margins, close to 137A. Color, lower surface: Close to N137A.

*Peduncles*.—Length: About 13.4 cm. Diameter: About 5 mm. Strength: Strong. Aspect: Upright to about 30° from vertical. Texture: Densely pubescent; strigose. Color: Close to 144A; peduncles exposed to direct sunlight are tinged with close to 200B.

*Reproductive organs*.—Androecium (present on ray and disc florets): Quantity per floret: Five. Filament length: About 3 mm. Filament color: Close to 150C. Anther length: About 3 mm. Anther shape: Lanceolate. Anther color: Close to 197A and 202A. Pollen amount: Moderate. Pollen color: Close to 15A. Gynoecium (present only on disc florets): Quantity per floret: One. Pistil length: About 7 mm. Stigma shape: Decurrent, unequal. Stigma color: Close to 187A. Style length: About 5.5 mm. Style color: Close to 150C. Ovary color: Close to 150D. Seeds and fruits: Seed and fruit development have not been observed on plants of the new *Echinacea*.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Apecssima' as illustrated and described.

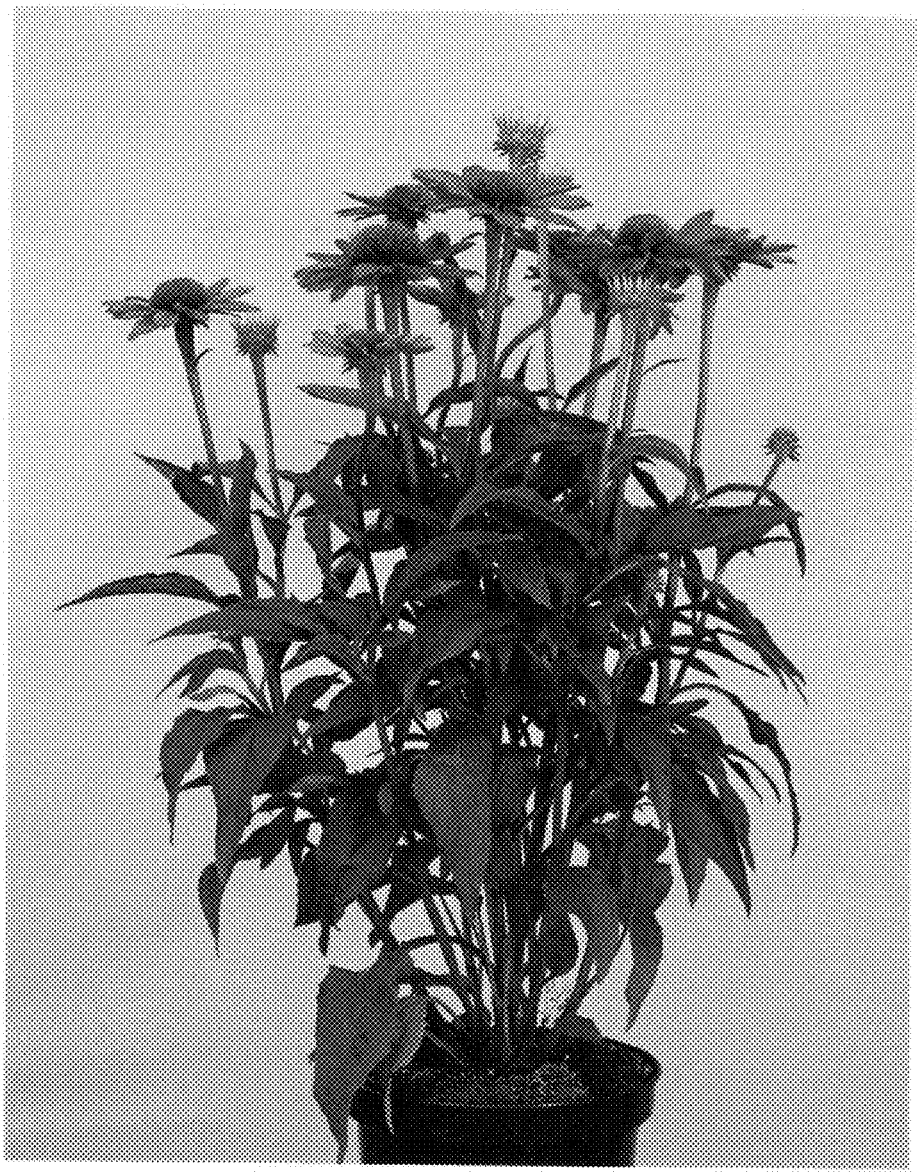

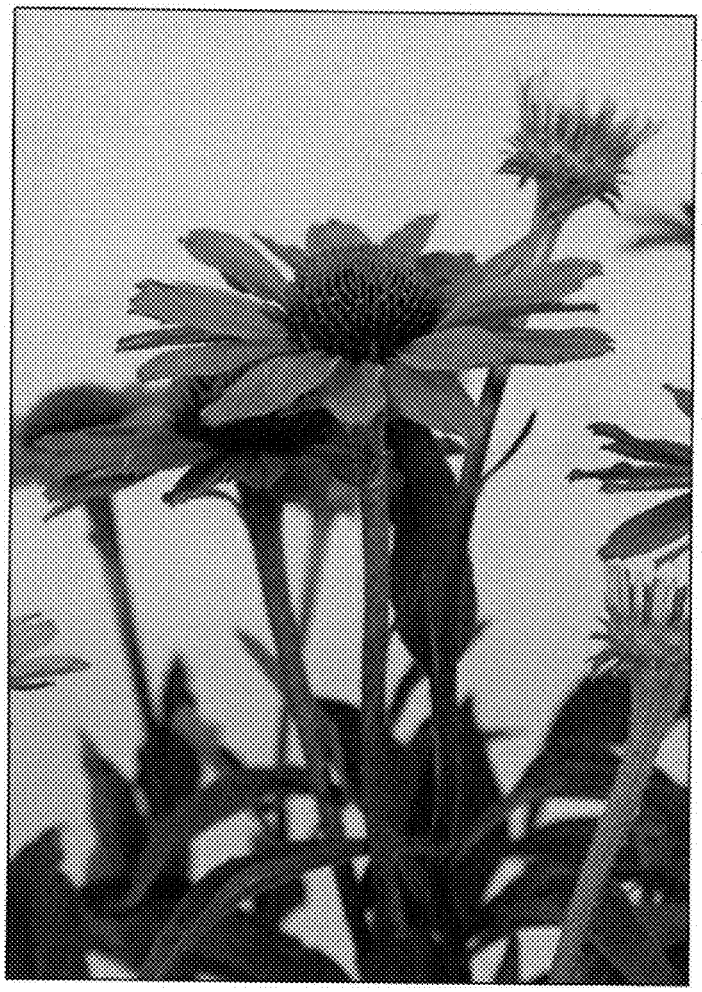
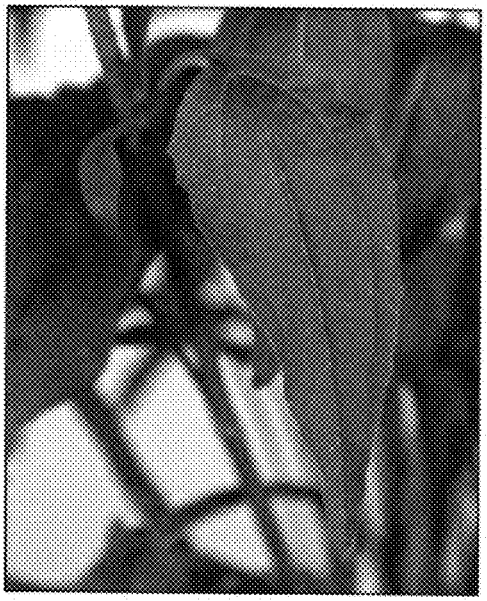

* * * * *